United States Patent [19]

Baldwin

[11] 4,436,740

[45] Mar. 13, 1984

[54] 3-CYCLOALKYLAMINO-2-OR-PROPOX-YCYANOPYRIDINES

[75] Inventor: John J. Baldwin, Gwynedd Valley, Pa.

[73] Assignee: Merck & Co., Inc., Rahway, N.J.

[21] Appl. No.: 401,454

[22] Filed: Jul. 26, 1982

[51] Int. Cl.³ .................... C07D 213/57; A61K 31/44
[52] U.S. Cl. ..................................... 424/263; 546/288
[58] Field of Search ......................... 546/288; 424/263

[56] References Cited

U.S. PATENT DOCUMENTS

| | | | |
|---|---|---|---|
| 3,657,237 | 4/1972 | Weinstock et al. | 544/134 |
| 3,718,647 | 2/1973 | Weinstock et al. | 544/134 |
| 4,000,282 | 12/1976 | Baldwin | 424/263 |
| 4,053,605 | 10/1977 | Baldwin | 424/263 |
| 4,115,575 | 9/1978 | Frei et al. | 424/250 |
| 4,144,343 | 3/1979 | Baldwin et al. | 424/263 |
| 4,145,425 | 3/1979 | Baldwin | 424/263 |
| 4,151,284 | 4/1979 | Baldwin | 424/263 |
| 4,294,969 | 10/1981 | Baldwin et al. | 546/286 |

*Primary Examiner*—Alan L. Rotman
*Attorney, Agent, or Firm*—Daniel T. Szura

[57] ABSTRACT

3-Cycloalkylamino-2-OR-propoxycyanopyridines having pharmacological activity are disclosed.

8 Claims, No Drawings

3-CYCLOALKYLAMINO-2-OR-PROPOX-YCYANOPYRIDINES

BACKGROUND OF THE INVENTION

The present invention is concerned with N-Alkylamino-OR-propoxycyanopyridines. These pyridines have useful pharmaceutical activity, e.g., as antihypertensive agents.

N-Alkyl-OR-propoxycyanopyridines are taught in U.S. Pat. Nos. 4,000,282, 4,053,605, 4,294,969, 4,144,343, 4,145,425 and 4,141,284 to be useful antihypertensive agents. These compounds also have β-adrenergic blocking activity. Certain N-substituted hydroxypropoxyheterocyclics are also disclosed in U.S. Pat. No. 4,115,575 and are taught, among other things, to have β-adrenergic blocking activity.

Novel cycloalkylamino-OR-propoxycyanopyridines which are useful as antihypertensive agents have been discovered.

SUMMARY OF THE INVENTION

3-Cycloalkylamino-2-OR-propoxycyanopyridines and their use as pharmaceutically active agents.

DETAILED DESCRIPTION OF THE INVENTION

An embodiment of the present invention is compounds having the formula:

$$R_a-O-CH_2-CHOR-CH_2-NHR_1$$

and pharmaceutically acceptable salts thereof wherein $R_a$ is

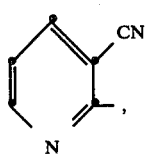

R is H or

wherein L is $C_1-C_{10}$ alkyl, phenyl or substituted having one or two substituents which are independently selected from $C_1-C_4$ alkyl, $C_1-C_4$ alkoxy or halo; and $R_1$ is indanyl, $C_5-C_8$ cycloalkyl or substituted $C_5-C_8$ cycloalkyl wherein the substituent is mono- or diloweralkyl.

R is H or the

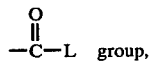

with H being preferred. The L group includes $C_1-C_{10}$, linear and branched hydrocarbon alkyl such as methyl, n-decyl, tert butyl, isoamyl, n-heptyl and the like with $C_1-C_4$ alkyl being preferred, and phenyl or mono- and disubstituted phenyl such as tert butylphenyl, 2,6-dibromophenyl, 3-methylphenyl, 4-n-propylphenyl, 3,5-dimethoxyphenyl, 4-iodophenyl, 2-methyl-4-chlorophenyl, 4-fluorophenyl and the like, with monosubstituted phenyl being preferred.

$R_1$ includes $C_5-C_8$ cycloalkyl groups namely cyclohexyl, cycloheptyl, cyclopentyl and cyclooctyl, mono- or diloweralyl substituted $C_5-C_8$ cycloalkyl wherein the loweralkyl group has 1-6 carbon atoms exemplified by:

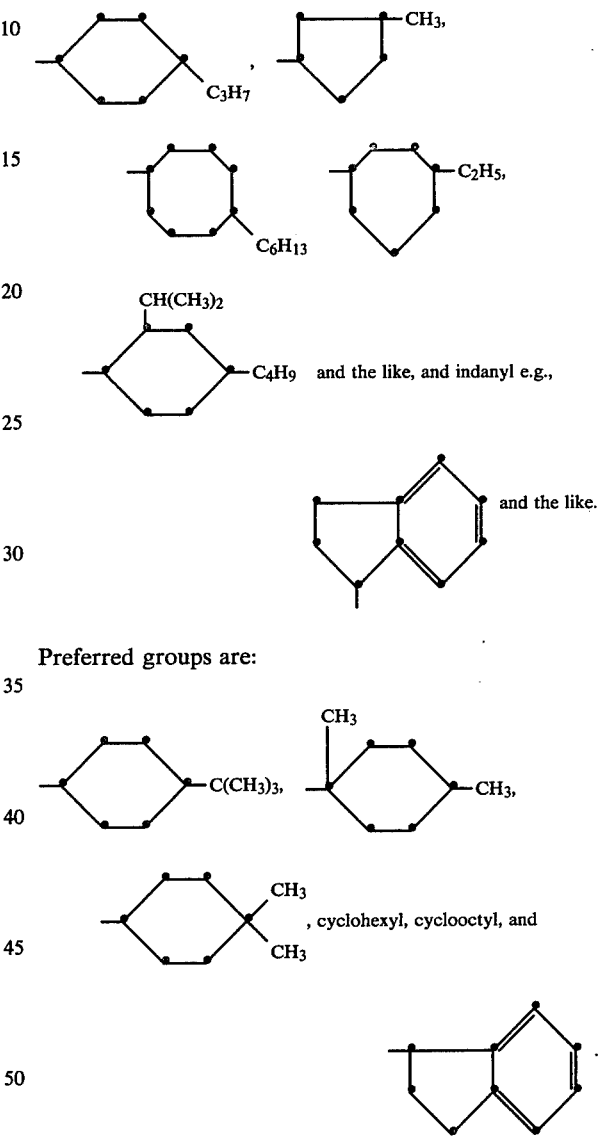

Preferred groups are:

More preferred $R_1$ groups are cyclooctyl,

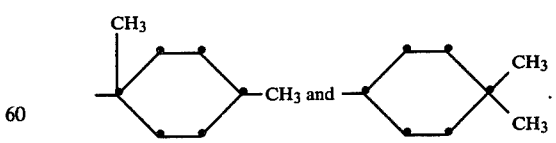

A most preferred $R_1$ group is cyclooctyl.

The compounds of the present invention also include the pharmaceutically acceptable salts of the Formula I pyridines. These salts are generally salts of the Formula I pyridines and organic or inorganic acids. These salts are prepared by treating the pyridine with an appropriate amount of a useful acid, generally in a suitable solvent. Examples of useful organic acids are isethionic acid and carboxylic acids such as maleic acid, acetic acid, succinic acid, pamoic acid, oxalic acid, pivalic acid and the like; useful inorganic acids are hydrohalo acids such as HCl, HBr, HI; sulfuric acid, phosphoric acid and the like. The hydrochloride and hydrogen maleate salts are examples of preferred salts.

The pyridines of Formula I have a chiral center at the 2-position in the propoxysubstituent, which confers optical activity. All the optical isomer forms, that is mixtures of enantiomers, e.g., racemates as well as the individual enantiomers of Formula I are included. These individual enantiomers of Formula I are commonly designated according to the optical rotation they effect by (+) and (−), (L) and (D), (l) and (d) or combinations of these symbols. These isomers may also be designated according to their absolute spatial configuration by (S) and (R) which stand for sinister and rectus, respectively. Where no symbol is used in naming a compound, the compound is a racemate. The (S) isomer is a preferred isomer configuration.

Pyridines of the present invention can be prepared by any convenient process.

One process involves the coupling of a halopyridine with a suitable substituted oxazolidine and hydrolyzing the reaction product obtained. This process is illustrated by the following set of reaction equations:

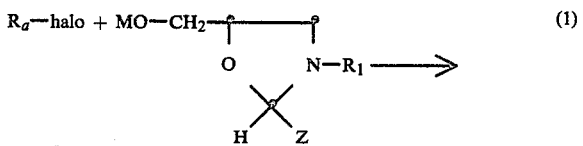

(1)

III

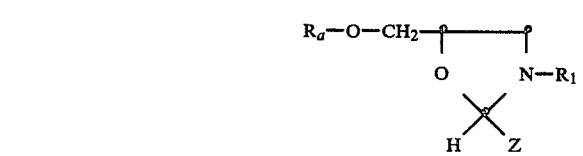

IV

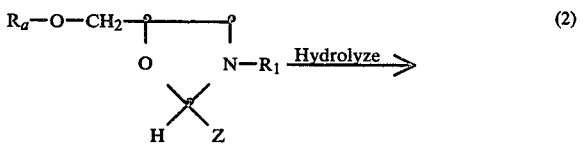

(2)

IV $$R_a-O-CH_2-CHOH-CH_2-\overset{H}{\underset{|}{N}}R_1$$

I'

Halo may be Cl, Br, F and I, with Cl being preferred. M is an alkali metal, with potassium or sodium. Z can be hydrogen or the residue of any suitable aldehyde

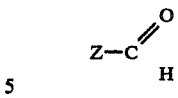

e.g., an arylaldehyde, such as benzaldehyde, naphthaldehyde and the like, or an alkanal such as acetaldehyde, butyraldehyde and the like. The process for preparing oxazolidines where M is hydrogen is disclosed in U.S. Pat. Nos. 3,718,647 and 3,657,237 and to the extent necessary the pertinent disclosure is incorporated herein by reference. The alkali metal salt of the oxazolidine is prepared in a conventional manner by reaction of the corresponding hydroxymethyloxazolidine with an appropriate amount of an alkali base reactant. However, this Reaction A may also be carried out with in-situ formation of the alkali metal oxazolidine salt (Formula III) by reacting the oxazolidine

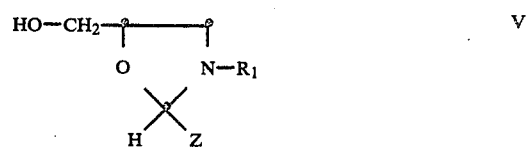

V with the Formula II pyridine in the presence of a strong base such as an alkali metal alkoxide (e.g., K—O—C—(CH₃)₃) or sodium hydride.

The coupling reaction can be carried out at temperatures ranging from about 0° C. to the reflux temperature of the solvent. A temperature range of about 10° C. to about 75° C. is preferred. The reaction is generally carried out in a solvent. Any suitable solvent may be used. Examples of useful solvents are dimethylformamide, dimethylsulfoxide, hexamethylphosphoramide, tert butanol, alkanols and the like. The hydrolysis is carried out using conventional acid hydrolysis reagent and techniques, e.g., treatment with a solution of an acid such as acetic acid or any strong mineral acid such as HCl or H₂SO₄. The hydrolysis product can be directly obtained as the salt of the acid used for the hydrolysis. Ordinarily, the product I is recovered as the free base after conventional neutralization of the salt.

The coupling reaction is ordinarily carried out at atmospheric pressure. Higher pressures may be used if desired.

When a racemic oxazolidine (Formula III or V) is used as a reactant, the product is obtained as a racemate. The racemate may be separated into its individual enantiomers by conventional resolution techniques, e.g., using an enantiomer of a suiable optically active organic acid such as tartaric acid.

When Z in the oxazolidine, i.e., Formula III, IV or V, is other than hydrogen, in addition to the chiral center at oxazolidine position 5 there is a second chiral center at position 2. However, whenever the oxazolidine is designated, e.g., as (S), (R) or (R,S), this designation refers only to the optical configuration around the carbon atom at the 5 position.

By using a single optical isomer of said oxazolidine in the above reactions, the product may be obtained directly as a single enantiomer. Thus, if the S-isomer of the oxazolidine is used, then the product obtained will be the S-isomer. This provides a convenient way for directly preparing individual isomers of the present pyridines.

Another convenient process for preparing the present pyridines is by treating an appropriate pyridine epoxide with a suitable amino as illustrated by the following reaction equation:

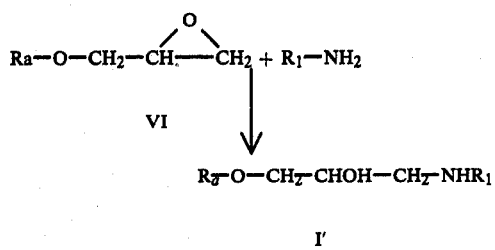

I'

This reaction is advantageously carried out in excess amine ($R_1NH_2$) reactant. Temperatures up to reflux can be used. An especially useful temperature range is room temperature to about 100° C. The reaction is conveniently carried out at room temperatures.

The product from the epoxide/$R_1NH_2$ reaction is ordinarily a racemate, and can be separated using conventional resolution procedures.

If a single optical isomer of the Formula VI epoxide is used, as the reactant, the product obtained is the corresponding single optical isomer, e.g.,

The optically active epoxide intermediates of Formula VI can be prepared by the reaction illustrated below:

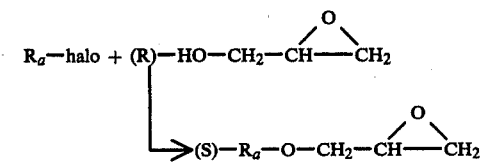

Pyridines of the present invention wherein R is other than hydrogen are conveniently prepared by treating the corresponding pyridine where R is hydrogen with an appropriate acylating agent such as an acyl halide, e.g., undecanoyl chloride, pivaloyl chloride, benzoyl-chloride, p-methoxybenzoyl chloride or an anhydride, e.g., acetic anhydride, and the like. The reaction is illustrated by the following equation:

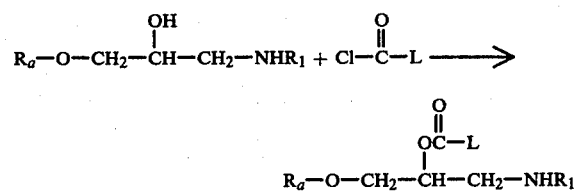

The compounds of the present invention have β-adrenergic blocking activity. This β-adrenergic blocking activity is determined by measuring the ability of representative pyridines to block the β-adrenergic stimulant effect of isoproterenol in a test animal.

The present pyridines also exhibit antihypertensive activity of immediate onset. This rapid onset antihypertensive activity is determined by administering a representative pyridine of the present invention to spontaneously hypertensive (SH) rats and measuring the effect on blood pressure.

The ability of the compounds of the present invention to reduce blood pressure in the SH rat indicates that the compounds and their salts may be useful to treat essential hypertension in humans.

The β-adrenergic blocking effectiveness of the present compounds indicates that they are useful in treating human cardiovascular conditions such as angina pectoris and arrhythmias, especially when effect on the pulmonary function must be minimized, e.g., in a patient who also has asthma.

For use as β-adrenergic blocking agents, and/or antihypertensive agents the compounds of the present invention can be administered orally, by inhalation, by suppository or parenterally, i.e., intravenously, intraperitoneally, etc., and in any suitable dosage form. The compounds may be offered in a form (1) for oral administeration, e.g., as tablets in combination with other compounding ingredients (diluents or carriers) customarily used such as talc, vegetable oils, polyols, benzyl alcohols, starches, gelatin and the like—or dissolved, dispersed or emulsified in a suitable liquid carrier—or in capsules or encapsulated in a suitable encapsulating material, or (2) for parenteral administration, dissolved, dispersed, or emulsified in a suitable liquid carrier or diluent or (3) as an aerosol or (4) as a suppository. The ratio of active ingredient (present pyridine) to compounding ingredients will vary as the dosage form requires. Conventional procedures are used to prepare the pharmaceutical formulations.

The effective daily dosage level for the present compounds may be varied from about 10 mg to about 2000 mg. Daily doses ranging from about 50 to about 1000 mg are preferred, with about 100 to about 500 mg being a more preferred range. Oral administration is preferred. Either single or multiple daily doses may be administered depending on unit dosage.

Thus, another embodiment of this invention is a pharmaceutical composition containing β-adrenergic blocking or antihypertensive amount of a compound of the present invention.

The following examples illustrate the preparation of representative compounds of the present invention. Temperatures are in °Celsius.

EXAMPLE 1

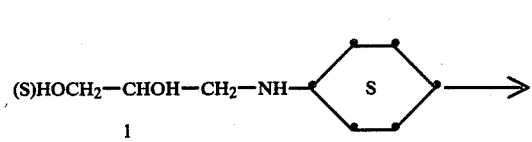

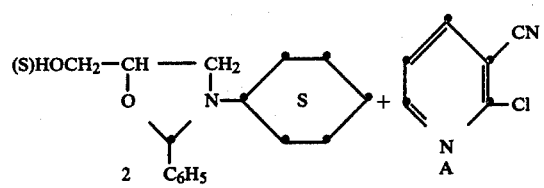

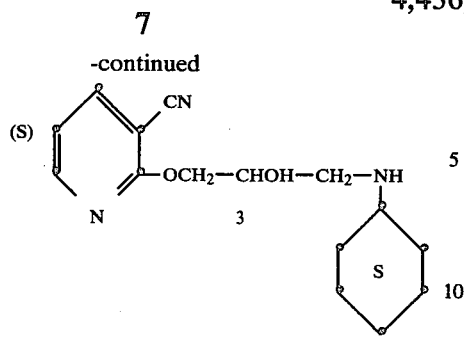

Preparation of 1

A solution of isopropylidene-(R)-glyceraldehyde (12.0 g, 0.092 mole) in THF (120 ml) is added dropwise over one hour during hydrogenation to a mixture of cyclohexylamine (27.37 g., 0.276 mole), methanol (70 ml) and 5% palladium on carbon (5 g). The mixture is hydrogenated at room temperature until hydrogen uptake ceases and then the catalyst is filtered off, washed with methanol, and the filtrate is concentrated. The residue is diluted with 6 N HCl (300 ml) and stirred on a steam bath for one hour. The aqueous solution is cooled to 0° C. and treated with NaOH (100 g) keeping the temperature below 30° C. The basic solution is diluted with H₂O (100 ml) and extracted with methylene chloride. The extract is dried, filtered, and concentrated and the residual oil is diluted with ethyl acetate (750 ml). The precipitate which forms is filtered and washed with cold ethyl acetate and the filtrate is concentrated. The residue is diluted with ethyl acetate and the precipitate which forms is filtered to yield 4.49 g of 1, m.p. 80°–82° C.

Preparation of 2

To a solution of benzene (15 ml), benzaldehyde (25 ml) and benzoic acid (250 mg) is added 1 (4.49 g, 0.0259 mole) and the resulting solution is refluxed for 6.5 hours with removal of water. After cooling to room temperature the reaction solution is diluted with benzene (25 ml) and washed successively with aqueous NaHCO and aqueous NaCl solutions. The organic layer is dried, filtered, and concentrated and the residue distilled to yield 3.8 g (56%) of oil (2) collected at 145°–165° C./0.05 mm Hg.

Preparation of 3

To a rapidly stirred solution of 2 (3.8 g, 0.0145 mole) in DMF (25 ml) is added sodium hydride (0.7 g of 50% mineral oil dispersion) under nitrogen. The reaction mixture is heated on a steam bath for 10 minutes and then stirred at room temperature for 30 minutes. A solution of 2-chloro-3-cyanopyridine A (2.01 g, 0.0145 mole) in DMF (10 ml) is added dropwise and the reaction mixture is stirred 16 hours at room temperature and then poured into ice H₂O (100 ml). The aqueous mixture is extracted with ethyl acetate and the extract is washed with H₂O and then extracted successively with 1.5 N HCl and H₂O and the combined extract is heated on a steam bath for 30 minutes and then stirred at room temperature for 30 minutes. The aqueous solution is extracted with benzene and then cooled in ice as solid Na₂CO₃ is added until the solution is basic to litmus. The basic solution is extracted with ethyl acetate and the extract is dried, filtered and concentrated. The residual solid is purified as the maleate salt from ethanol/ethyl acetate to yield 1.74 g of pure 3 maleate, m.p. 130°–134° C.

EXAMPLE 2

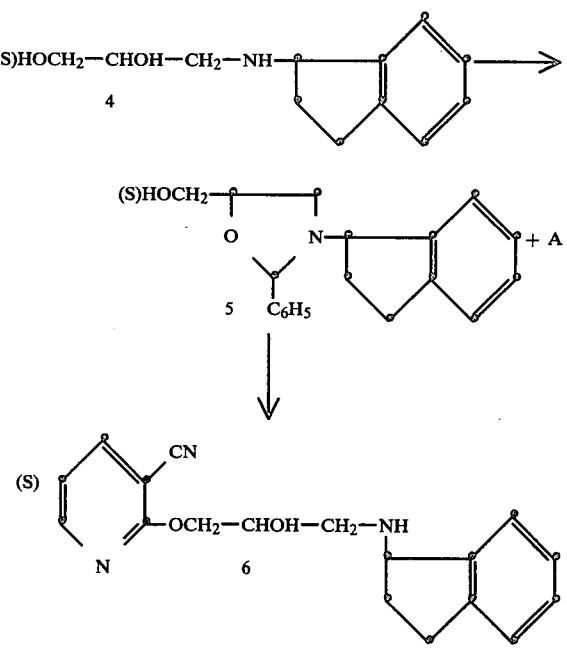

Preparation of 4

Following the procedure for the preparation of compound 1 and substituting 1-aminoindan for cyclohexylamine, compound 4 is prepared and purified by distillation, B.P.$_{0.2\ mm}$ 170°–175° C.

Preparation of 5

Following the procedure for the preparation of compound 2 and substituting compound 4 for compound 1, compound 5 is prepared in 39% yield, B.P.$_{0.02}$ 185°–195° C.

Preparation of 6

Following the procedure for the preparation of compound 3 and substituting compound 5 for compound 2, compound 6 is prepared and purified as the hydrochloride salt from ethanol/ethyl acetate, m.p. 130°–132° C.

EXAMPLE 3

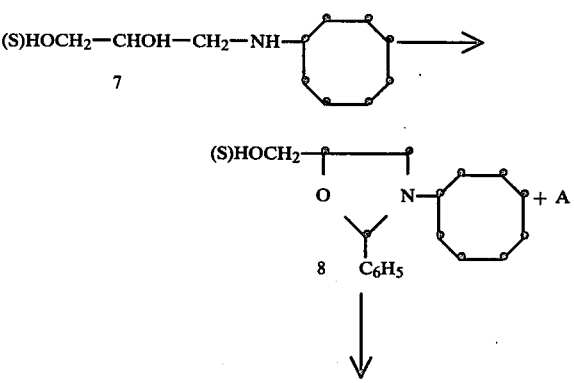

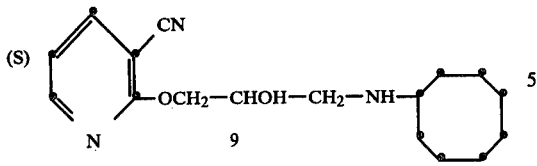

Preparation of 7

Following the procedure for the preparation of compound 1 and substituting cyclooctylamine for cyclohexylamine, compound 7 is prepared and purified by distillation, B.P.$_{0.02\ mm}$ 160°–168° C.

Preparation of 8

Following the procedure for the preparation of compound 2 and substituting compound 7 for compound 1, compound 8 is prepared, B.P.$_{0.2\ mm}$ 180°–188° C.

Preparation of 9

Following the procedure for the preparation of compound 3 and substituting compound 8 for compound 2, compound 9 is prepared and purified as the hydrochloride salt from ethanol/ethyl acetate, m.p. 144°–146° C.

Other formula I compounds prepared using substantially the same procedures as directed in the above example were

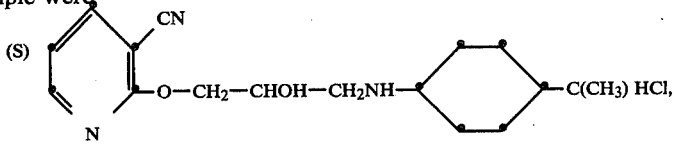

m.p. = 161°–164° C.;

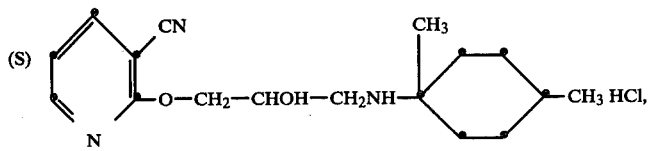

m.p. = 165°–167° C.; and

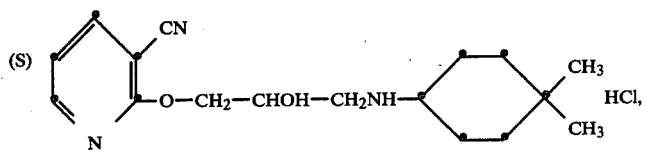

m.p. = 189°–190° C.

Claims to the invention follow.
What is claimed is:
1. Compounds having the formula:

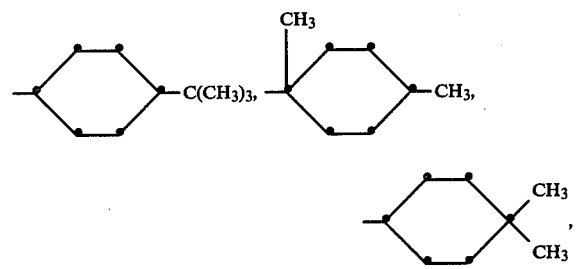

and pharmaceutically acceptable salts thereof wherein:
R is H and
R$_1$ is C$_5$–C$_8$ cycloalkyl or substituted C$_5$–C$_8$ cycloalkyl wherein the substituent is mono- or diloweralkyl.

2. Compounds of claim 1 wherein R is H.

3. Compounds of claim 2 wherein R$_1$ is C$_5$–C$_8$ cycloalkyl or substituted C$_5$–C$_8$ cycloalkyl.

4. Compounds of claim 3 wherein R$_1$ is cyclohexyl or cyclooctyl.

5. Compounds of claim 4 wherein R$_1$ is cyclooctyl,

6. Compounds of claim 5 wherein R$_1$ is cyclooctyl.

7. A pharmaceutical composition for treating hypertension comprising an effective amount of compound of claim 1.

8. A method of treating hypertension in humans by administering to humans in need of such treatment, an effective amount of a compound of claim 1.

* * * * *